United States Patent [19]

VandenBerg

[11] Patent Number: Plant 6,948

[45] Date of Patent: Jul. 25, 1989

[54] CHRYSANTHEMUM PLANT NAMED FONTANA

[75] Inventor: Cornelis P. VandenBerg, Salinas, Calif.

[73] Assignee: Yoder Brothers, Inc., Barberton, Ohio

[21] Appl. No.: 218,881

[22] Filed: Jul. 14, 1988

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Fontana particularly characterized by its flat capitulum form; spooned decorative capitulum type; yellow ray floret color; diameter across face of capitulum of up to 15 cm at maturity when grown as a pinched disbudded pot mum; uniform eight week photoperiodic flowering response to short days; short plant height when grown as a pinched pot mum; recommended as disbudded pot mum; spreading and prolific branching pattern.

3 Drawing Sheets

The present invention comprises a new and distinct cultivar of Chrysanthemum, botanically known as *Dendranthema grandiflora,* and referred to by a cultivar name Fontana.

Fontana, identified as 82208018, was originated from a cross made by Cornelis P. VandenBerg in a controlled breeding program in Salinas, Calif. in 1982.

The female parent of Fontana was an unnamed seedling identified as 77423014. The male parent of Fontana was an unnamed seedling identified as 80032001.

Fontana was discovered and selected as one flowering plant within the progeny of the stated cross by Cornelis P. VandenBerg in December 1982 in a controlled environment in Salinas, Calif.

The first act of asexual reproduction of Fontana was accomplished when vegetative cuttings were taken from the initial selection in March 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Fontana are firmly fixed and are retained through successive generations of asexual reproduction.

Fontana has not been observed under all possible environmental conditions. The phenotype may vary significantly with variations in environment such as temperature, light intensity, and daylength.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Fontana, which, in combination, distinguish this Chrysanthemum as a new and distinct cultivar:

1. Flat capitulum form.
2. Spooned decorative capitulum type.
3. Yellow ray floret color.
4. Diameter across face of capitulum up to 15 cm at maturity when grown as a pinched disbudded pot mum.

5. Uniform eight week photoperiodic flowering response to short days.
6. Short plant height, requiring 7 to 14 long days after pinch prior to short days and 1 application of 2500 ppm B-9 SP to attain a flowered plant height of 25 to 35 cm for year-round flowerings when grown as a pinched pot mum.
7. Recommended as disbudded pot mum.
8. Spreading and prolific branching pattern.

The accompanying photographic drawings show typical inflorescence and leaf characteristics of Fontana, with the colors being as nearly true as possible with illustrations of this type.

Sheet 1 is a color photograph of Fontana grown as a pinched disbudded pot mum.

Sheet 2 is a black and white photograph of three views of the inflorescence of Fontana.

Sheet 3 is a black and white photograph showing the upper and under sides of the leaves of Fontana at three stages of development (mature, intermediate and immature).

Of the commercial cultivars known to the inventor, the most similar in comparison to Fontana is Jasmine, disclosed in U.S. Plant Pat. No. 4,273. Reference is made to Chart A, which compares certain characteristics of Fontana to the same characteristics of Jasmine.

Similar traits are ray floret color and capitulum form and type. Fontana has a more spreading and prolific branching pattern, a slightly smaller diameter of capitulum, shorter plant height and a shorter flowering response period than Jasmine.

In the following description, color references are made to The Royal Horticultural Society Colour Chart. The color values were determined on plant material grown as a pinched disbudded pot mum in Salinas, Calif. on Mar. 14, 1988.

Classification:

*Botanical.*—*Dendranthema grandiflora,* cv. Fontana.

*Commercial.*—Spooned decorative disbud pot mum.

INFLORESCENCE

A. Capitulum:

*Form.*—Flat.

*Type.*—Spooned decorative.

*Diameter across face.*—Up to 15 cm at maturity.

B. Corolla of ray florets:

*Color (general tonality from a distance of three meters).*—Yellow.

*Color (upper surface) (spooned tips).*—6A.

*Color (under surface) (tubes).*—8A.

*Shape.*—Base tubular. Distal portion open, flattened and spoon like. Spoon length is small and varying, ranging from approximately 0% to 10% of the length of the ray floret.

C. Corolla of disc florets:

*Color (mature).*—Closest to 9A.

*Color (immature).*—Closest to 144A to 144B. At marketing stage disc florets are covered by the inner rows of ray florets.

D. Reproductive organs:

*Androecium.*—Present on disc florets only; scant pollen.

*Gynoecium.*—Present on both ray and disc florets.

PLANT

A. General appearance:

*Height.*—Short; 25 to 35 cm as a pinched pot mum with 7 to 14 long days after pinch prior to short days and 1 application of 2500 ppm B-9 SP.

*Branching pattern.*—Spreading and prolific.

B. Foliage:

*Color (upper surface).*—137A to 147A.

*Color (under surface).*—147B.

*Shape.*—Lobed and slightly serrated.

CHART A

COMPARISON OF FONTANA AND JASMINE

| | Fontana | Jasmine |
|---|---|---|
| Ray floret color | Yellow | Yellow |
| Capitulum form and type | Flat<br>Spooned<br>Decorative | Flat<br>Spooned<br>Decorative |
| Branching pattern | Spreading and prolific | Semi-spreading |
| Diameter across face of capitulum | Up to 15 cm | 140 to 160 mm |
| Plant height | Short | Medium |
| Flowering response period | 8 weeks | 9 weeks |

COMPARISONS MADE OF PLANTS GROWN AS PINCHED POT MUMS IN SALINAS, CALIFORNIA

I claim:

1. A new and distinct Chrysanthemum plant named Fontana, as described and illustrated.

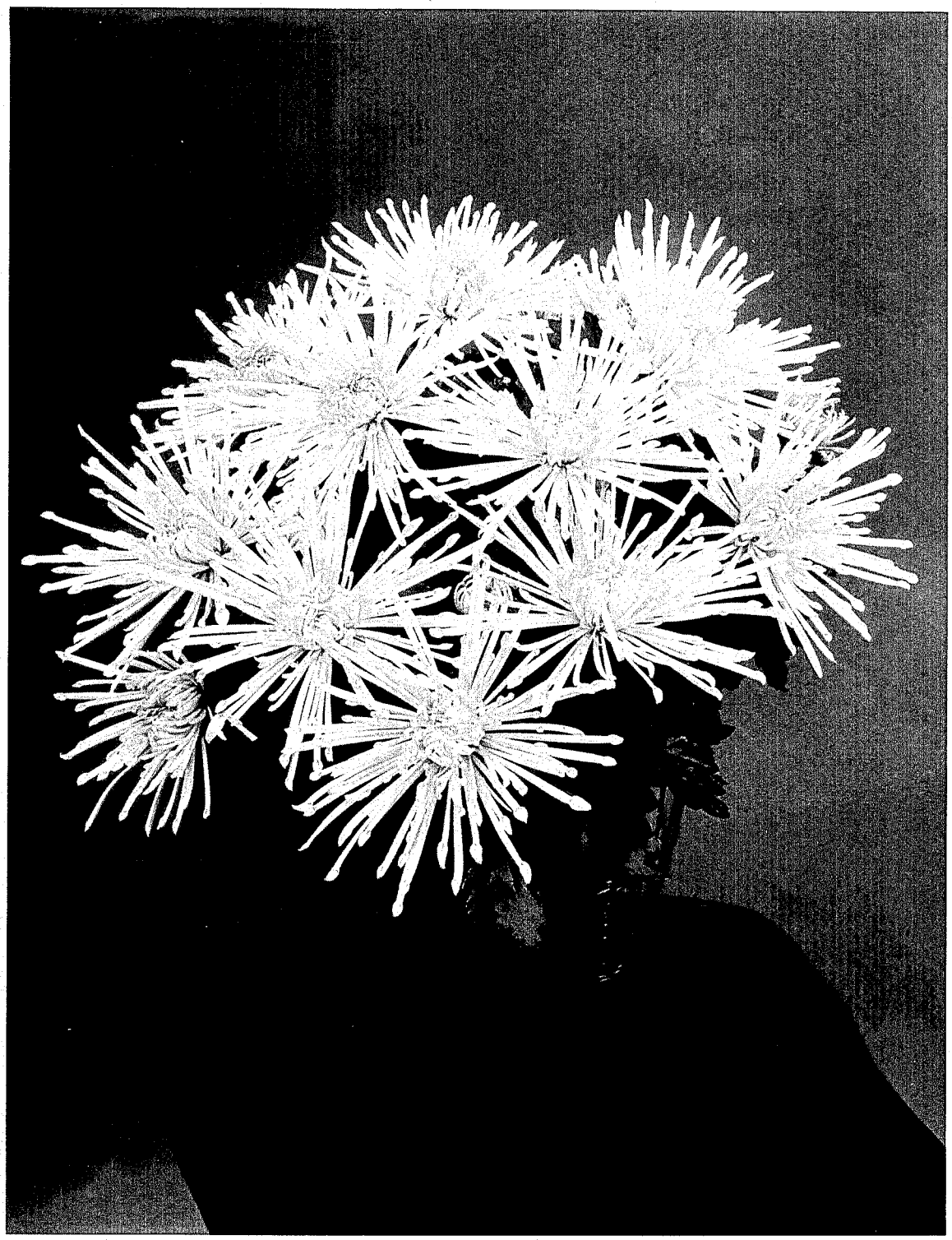

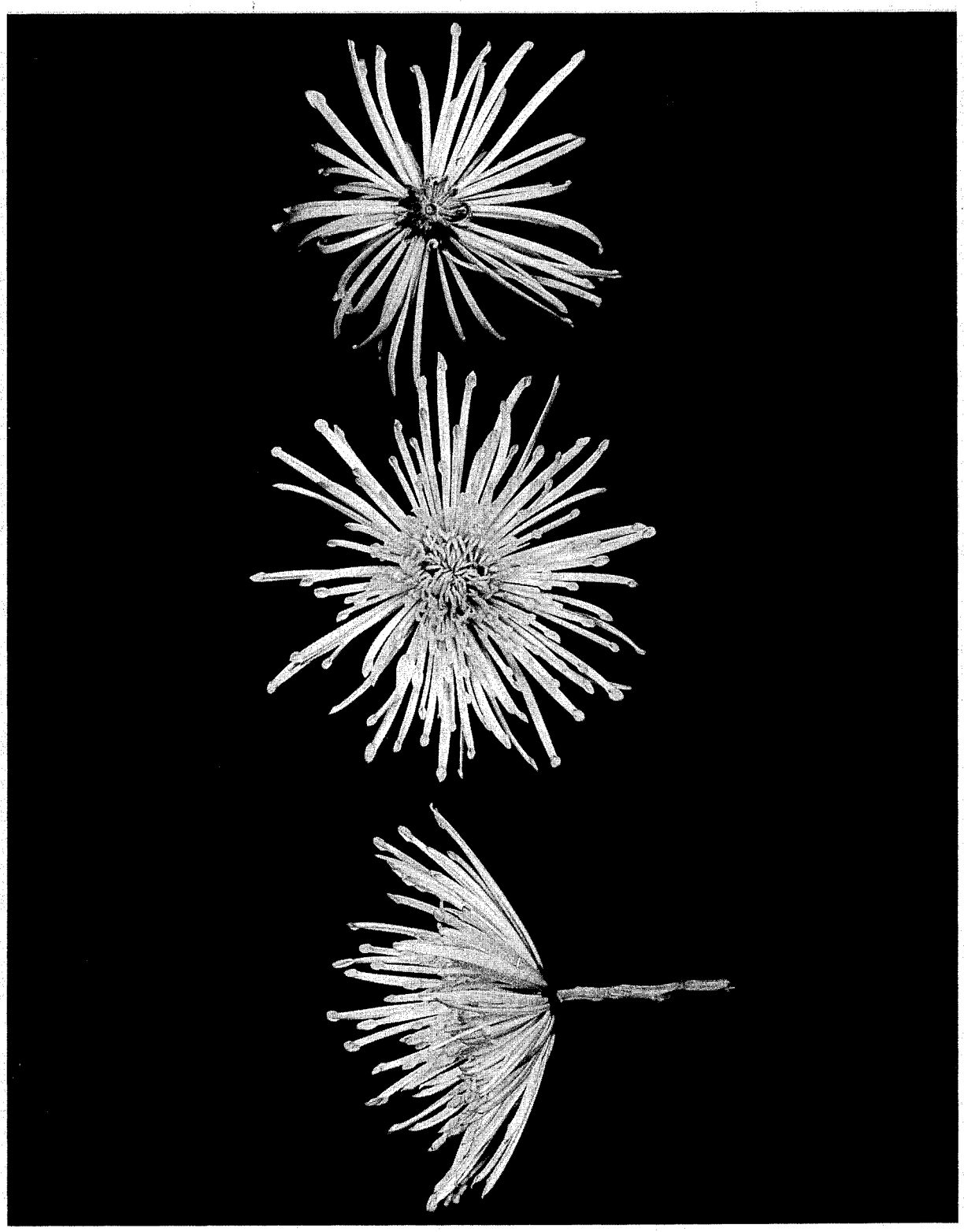

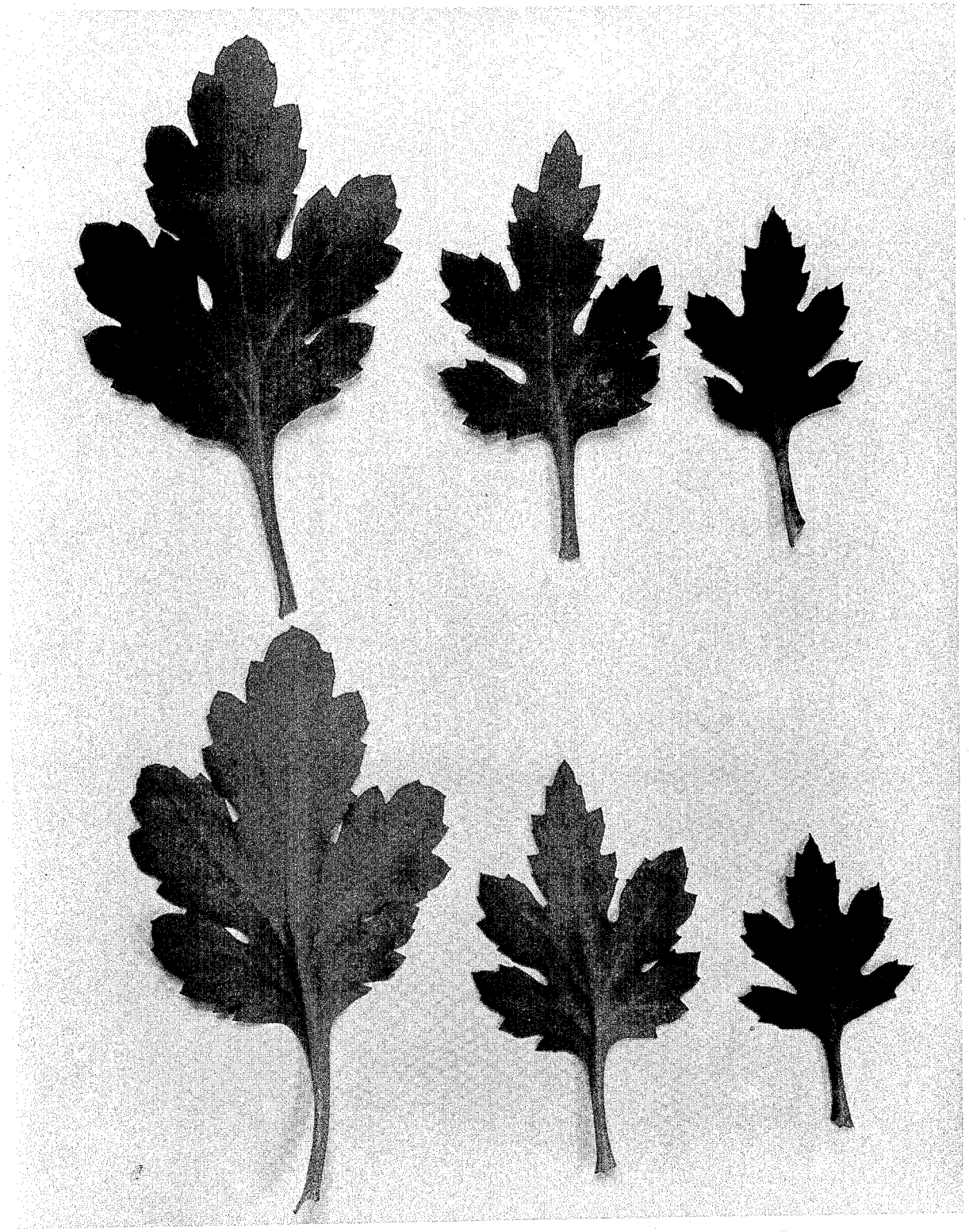

* * * * *